United States Patent [19]
Mori et al.

[11] Patent Number: 6,123,726
[45] Date of Patent: Sep. 26, 2000

[54] PORTABLE DRIVE SYSTEM FOR ARTIFICIAL HEART

[75] Inventors: Toshio Mori, Chino; Kenji Yamazaki, Koganei; Koji Higuchi, Okaya; Keiichi Kaneko, Suwa, all of Japan

[73] Assignees: Seiko Epson Corporation, Tokyo; Sun Medical Technology Research Corporation, Suwa, both of Japan

[21] Appl. No.: 09/147,996

[22] PCT Filed: Jan. 26, 1998

[86] PCT No.: PCT/JP98/00319

§ 371 Date: Mar. 24, 1999

§ 102(e) Date: Mar. 24, 1999

[87] PCT Pub. No.: WO99/04834

PCT Pub. Date: Feb. 4, 1999

[30] Foreign Application Priority Data

Jul. 25, 1997 [JP] Japan .................................. 9-200638

[51] Int. Cl.$^7$ ...................................... A61M 1/10
[52] U.S. Cl. ........................... 623/3.27; 623/3.13; 600/17
[58] Field of Search .................... 623/3.1, 3.13, 623/3.27, 3.15; 600/16, 17

[56] References Cited

U.S. PATENT DOCUMENTS

| | | | |
|---|---|---|---|
| 4,704,121 | 11/1987 | Moise | 623/3.13 |
| 4,756,302 | 7/1988 | Portner et al. | 600/17 |
| 5,020,516 | 6/1991 | Biondi et al. | 600/17 |
| 5,041,086 | 8/1991 | Koening et al. | |
| 5,147,392 | 9/1992 | Inagaki et al. | 623/3.1 |
| 5,501,216 | 3/1996 | Byrd | |
| 5,599,311 | 2/1997 | Raulerson | |
| 5,693,091 | 12/1997 | Larson, Jr. et al. | |
| 5,755,784 | 5/1998 | Jarvik | 623/3.1 |
| 5,776,110 | 7/1998 | Guy et al. | |

FOREIGN PATENT DOCUMENTS

WO 90/15640  12/1990  WIPO .

*Primary Examiner*—Bruce Snow
*Attorney, Agent, or Firm*—Mark P. Watson

[57] ABSTRACT

A portable drive system for an artificial heart can be provided that includes a blood pump 1 having a blood seal for sealing a rotation shaft 13, a system drive section 45 including a purge solution circulator 20 for supplying by circulating purge solution to the blood seal 18, a pump controller 30 for driving the blood pump 1, a power supply means 33 for supplying electric power thereto, a display 40 for displaying operating states thereof, a communication interface 50 for transmitting information to the outside, and a controller means 100 for controlling these components, a portable transport section 60 for bearing the system drive section 45, and a connecting section 70 for connecting the blood pump 1 and the system drive section 45. The portable artificial-heart drive system has high safety and high reliability, is small-sized, lightweight and easy to use, and can expand the range of life.

33 Claims, 9 Drawing Sheets

PORTABLE DRIVE SYSTEM FOR ARTIFICIAL HEART

BACKGROUND OF THE INVENTION

1. Technical Field

The present invention relates to medical equipment for use in a human body, and more particularly, to a portable drive system for an artificial heart, and to a portable drive system for an artificial heart that has high safety, high reliability, and reduced size and weight, and is easy to use, thereby expanding the range of life.

2. Background Art

Since a conventional drive system for an artificial heart is large and difficult to move, the life of a patient using the artificial heart has been limited to the inside of a hospital. While attempts have recently been made to reduce the size of an artificial-heart drive system, a system to be used in life outside a hospital is not yet in actual use in terms of size and safety.

An artificial-heart drive system is large, and therefore, the life of the patient is limited to the inside of the hospital. In terms of improved quality of life for the patient and medical rehabilitation, it is preferable that the life of the patient be not limited and that the patient can live a life at home. For that purpose, it is necessary to reduce the size of attendant fixtures of the artificial heart, to improve reliability, and to establish safeguards.

Accordingly, the present invention has been made in view of such circumstances, and has as an object the provision of a drive system for an artificial heart that does not limit the life of a patient having an implanted artificial heart with much regard for high safety.

DISCLOSURE OF INVENTION

A portable drive system for an artificial heart according to the present invention includes a blood pump 1 to be implanted in a body, a system drive section 45 for controlling the blood pump 1 from outside the body, and a connecting section 70 for connecting the blood pump 1 or purge solution circulating means and the system drive section 45. The connecting section 70 penetrates through the epidermis F of a patient.

The system drive a purge solution circulator 20 or a purge solution circulating means for supplying by circulating solution (hereinafter referred to as purge solution) to a contact surface of a blood seal 18 located inside the blood pump 1 in order to maintain the shaft sealing of a rotation shaft 13 in the blood pump 1 with respect to blood, a pump controller 30 pump control means for electrically controlling the drive of the blood pump 1 via. a motor cable 71, a display 40 or display means for displaying operation states of the aforementioned means and data thereon, a communication interface 50 or communication means for exchanging information with the outside, a power supply 33 or power supply means for supplying electric power to the aforementioned means, a controller 100 or control means for controlling the aforesaid means, and a transport section 60 for bearing the system drive section 45 portably.

The blood seal 18 includes a contact seal, such as a mechanical seal and an oil seal.

The connecting section 70 includes purge tubes 24 and 25 for connecting the blood pump 1 and the purge solution circulator 20 and causing the purge solution to circulate between the purge solution circulator 20 and the contact surface of the blood seal 18, and the motor cable 71 for supplying electric power to the blood pump 1, a connecting terminal 80 for connecting internally embedded parts and externally exposed parts of the purge tubes 24 and 25 and the motor cable 71, a skin button section 90 for causing parts of the purge tubes 24 and 25 and the motor cable 71, which penetrate through the epidermis F, to firmly adhere to the epidermis F, a valve mechanism 75 for blocking the flow of the purge solution, and a protective tube 72 for covering the externally exposed parts of the purge tubes 24 and 25 and the motor cable 71.

The system drive section 45 has a plurality of pump controller 30 and a plurality of power supply 33, and at least one pair of the pump controller 30 and the power supply means 33 are located inside or near the connecting terminal 80.

The system drive section 45 further has a mechanism for supplying power only to the above pump controller 30 when the quantity of electricity remaining in the power supply 33 falls below a specified value.

The purge solution circulator 20 includes a purge solution circulating pump 22 for circulating the purge solution that circulates inside the blood pump 1 and a disinfectant to be added in the purge solution, a flexible reservoir 21 for storing the purge solution, a filter 23 for filtering the purge solution, and a bypass channel 26 located on the flow channel of the purge solution.

Also located on the flow channel of the purge solution are detectors for detecting the temperature and pressure of the purge solution, and the valve mechanism 75 for preventing the outflow of the purge solution.

The controller 100 has a kinetic load detecting mechanism 31 for detecting the kinetic load needed for the movement of the transport section 60, and has the function of controlling the number of revolutions of the blood pump 1 in accordance with the output from the detecting mechanism. The controller 100 also has the self diagnosis function of monitoring output signals from the constituents of the portable drive system and detecting the abnormal conditions of the constituents, and has means for transmitting control signals to the aforementioned means.

The display 40 has a monitor for displaying information obtained from output signals from the controller 100, and a control button 42 for changing operating parameters of the constituents.

The communication interface 50 has a transmission function of transmitting information about the operating state of the portable artificial-heart drive system to a control center of the hospital or the like, and a receive function of receiving instructions from the control center.

The connecting section 70 has an expandable structure, and a structure for reinforcing the protective tube 72 to prevent breakage.

The skin button section 90 has a structure in which the connecting section 70 firmly adheres to the epidermis F to prevent percutaneous infection and separation due to the movement of the body.

The portable artificial-heart drive system according to the present invention operates as follows.

First, according to the invention claimed in claim 1, a system drive section, which includes purge solution circulator for maintaining the shaft sealing of a rotation shaft of a blood pump with respect to blood, pump controller for electrically controlling the drive of the blood pump, display for displaying operating states of constituents of the portable artificial-heart drive system and inputting the conditions of the constituents, power supply for supplying electric power to the means, communication interface for exchanging information with the outside, and controller for controlling the means, is constructed in a compact size, mounted on a movable transport section, and connected to the blood pump implanted in the body via a connecting section. This makes it possible to obtain a portable artificial-heart drive system that is small-sized, lightweight, and movable, and to expand the life range of the patient.

According to the invention claimed in claim 2, a mechanical seal or an oil seal is used as a blood seal. By supplying the purge solution by circulating to a contact surface of the blood seal by the purge solution circulator, the lubrication of the contact surface is stabilized, and the sealing ability is maintained for a long time. Furthermore, since the contact surface of the blood seal is cooled, the contact surface is not damaged by heat denaturation of protein ingredients of the blood that enter the contact surface by diffusion. Still furthermore, since the blood ingredients that enter in the purge solution by diffusion are diluted and discharged outside the blood pump by a large amount of purge solution, the rotation shaft does not stick. The purge solution only circulates in the purge solution channel, and leaks from the blood seal portion in very small amounts.

According to the invention claimed in claims 3 and 4, when the quantity of electricity remaining in a battery built in the power supply falls below a specified value, power is preferentially supplied to the backup pump controller. This makes the driving time of the portable artificial-heart drive system longer, and thereby improves safety.

According to the invention claimed in claims 5 and 6, the portable artificial-heart drive system has a plurality of systems of pump controller and power supply serving as basic functions for the operation of the blood pump, which improves the safety of the portable artificial-heart drive system. Moreover, since at least one system of pump controller and power supply are separated from the transport section, and located near the surface of the patient's body, the blood pump is prevented from stopping even when serious trouble, such as the breakage of the transport section, or the cutoff of the connecting section, occurs. Therefore, the safety of the portable artificial-heart drive system is further improved.

According to the invention claimed in claims 7 and 8, since a filter using an ultrafilter membrane is located on the channel in which the purge solution circulates, it is possible to always keep the purge solution clean, to prevent the blood from coagulating at the seal and the bearing in the blood pump of the artificial heart, and simultaneously, to keep the purge solution sterilized and detoxified. By adding a disinfectant in the purge solution, the insides of the reservoir and the ultrafilter can be disinfected. Thereby, the purge solution that flows in the blood pump of the artificial heart is physically and chemically disinfected, and double safeguards are provided.

According to the invention claimed in claim 9, a cross flow circulation route having a bypass channel is formed to prevent the ultrafilter from clogging, and provides the following functions.

1. Since air in the filter is automatically removed via the bypass channel, the filter does not cause malfunction due to an air trap.

2. Since the bypass channel serves as a safety valve, the increase in pressure of the purge solution can be kept at a fixed value or less.

3. Because of the cross flow circulation route, the flow rate of the purge solution flowing in the purge solution circulator located outside the body increases by an amount corresponding to the flow rate of the purge solution passing through the bypass channel, and the radiation effect of the purge solution improves.

According to the invention claimed in claim 10, the reservoir, the purge solution circulating pump, and the ultrafilter may be combined into a unit so as to make periodical replacement thereof considerably easy and clean.

According to the invention claimed in claim 11, since the reservoir is made flexible, it can flexibly respond to its change in capacity with the outflow of purge solution via the contact surface of the blood pump, in altitude with the movement of the transport section, vibrations and the like, whereby the circulation of purge solution can be kept safe.

According to the invention claimed in claim 12, sensors for detecting the pressure are disposed at the entrance and exit of the filter to monitor the pressure, which makes it possible to detect the choking of the purge solution circulating circuit, the clogging of the filter, and the like.

According to the invention claimed in claim 13, a sensor for detecting the temperature is disposed on the purge tube to measure the temperature of the purge solution, which provides the following functions.

1. The safety of the portable artificial-heart drive system can be improved by controlling the temperature of the purge solution by changing the amount of the purge solution to be circulated so that the temperature does not reach the heat denaturation temperature of protein ingredients of blood.

2. A portable artificial-heart drive system that imposes little load on a living body can be constructed by controlling the flow rate of the purge solution so as to reduce the change of amount of heat between the living body and the portable artificial-heart drive system.

According to the invention claimed in claims 14 to 19, a mechanism for detecting the kinetic load of the patient is disposed to control the number of revolutions of the blood pump in accordance with the load, whereby the quality of life of the patient can be improved.

The kinetic load can be easily detected by calculating the moving speed of the transport section by a rotary detector disposed on a wheel of the transport section. Moreover, the number of revolutions of the blood pump can be changed in accordance with the heart rate of the living body to be estimated from the load change cycle of the blood pump that synchronizes with the heart rate. While these methods may be separately used, the use of both methods makes it possible to distinguish the change in heart rate due to the kinetic load and the change in heart rate due to medical strain, excitation or the like, and to thereby control the blood pump more closely. This can improve the quality of life of the patient.

According to the invention claimed in claims 20 and 21, the constituents of the artificial heart may be provided with sensors, and the operating states of the constituents are always displayed and monitored by using the display. When the value obtained from the sensor is compared with and deviates from the preset value, an alarm is given, and detailed information is displayed on the display. Furthermore, the information is transferred to the external control center via the communication interface, and appropriate instructions are transferred back from the external control center, which ensures that the patient has a safe life outside the hospital.

According to the invention claimed in claim 22, the internally embedded part and the externally exposed part of the connecting section are connected by the connecting terminal, and the connecting terminal is fixed to a belt-like stomach band. Therefore, external force caused by movement of the body is not directly transmitted to the internally embedded part of the connecting section. Moreover, since the connecting section can split at the connecting terminal, easy replacement and maintenance of the transport section are possible.

According to the invention claimed in claims 23 to 25, the connecting section is expandable and does not hinder the activities of the patient. Moreover, the purge tubes and the motor cable are prevented from breaking by being covered with a reinforced protective tube. Since the expansion amount of the protective tube is smaller than that of the purge tubes and the motor cable, the purge tubes and the motor cable are prevented from tensile fracture.

According to the invention claimed in claims 26 and 27, if the circulation of purge solution stops due to trouble or the like of the purge solution circulator, the valves disposed in the purge tubes are automatically closed, so that the purge solution is prevented from flowing out on the back of the blood seal in the blood pump. Therefore, it is possible to safely maintain the shaft sealing action of the blood seal. Considering that the externally exposed part of the portable artificial-heart drive system has a high risk of being damaged, the valve mechanism is placed in the internally embedded part to further improve the safety.

According to the invention claimed in claim 28, it is preferable that one system of the pump controller and the power supply be placed between the connecting terminal and the internally embedded part whose risk of damage is low.

According to the invention claimed in claim 29, a skin button section formed of carbon fibers having many pores on their surfaces is disposed in a part of the internally embedded part of the connecting section that penetrates through the epidermis, so that the skin button section firmly adheres to the epidermis, and percutaneous infection is avoided.

According to the invention claimed in claims 30 to 32, the means disposed outside the human body are carried on the transport section and can be transported along with the human body. The means also have a waterproof and anti-contamination structure, and a structure for absorbing vibrations and impacts caused by transportation, which improves the safety of the transport section.

According to the invention claimed in claim 33, the power supply of the transport section may be driven by AC power source, a power source installed in an automobile or the like, or a second battery built in the transport section, and this does not limit the scope of activities of the patient.

BEST MODE FOR CARRYING OUT THE INVENTION

A description will be given of an embodiment of the present invention which applies to an artificial heart.

Figure 1:
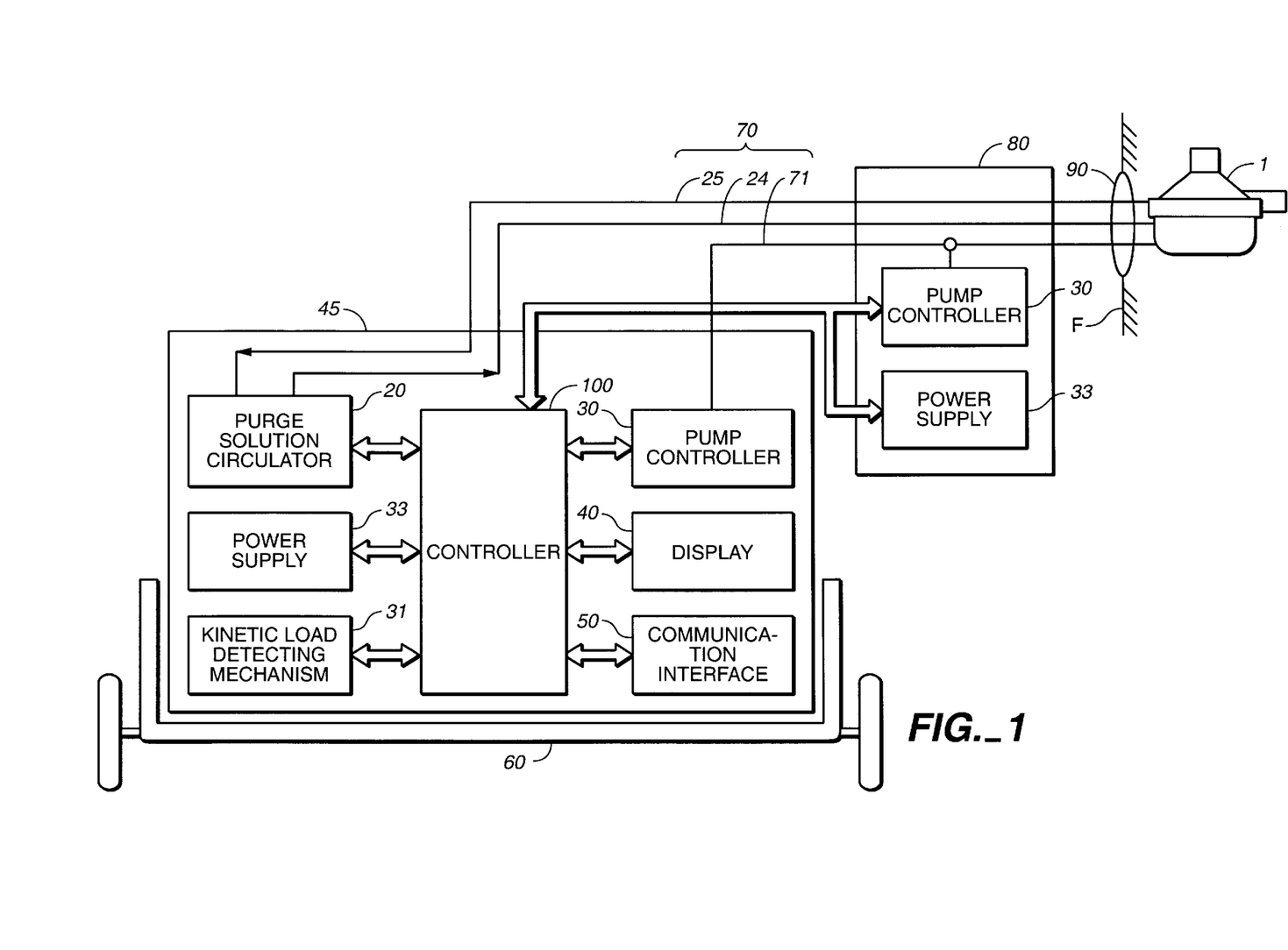
FIG. 1 is a structural diagram of a portable drive system for an artificial heart according to an embodiment of the present invention.

FIG. 1 is a structural diagram of a portable drive system for an artificial heart according to an embodiment of the present invention. In the figure, the portable artificial-heart drive system includes a blood pump 1 to be implanted in a body, a system drive section 45 for controlling the blood pump 1 from outside the body, and a connecting section 70 for connecting the blood pump 1 and the system drive section 45.

The portable artificial-heart drive system further includes the system drive section 45 that is composed of a purge solution circulator 20 for supplying by circulating purge solution to a contact portion of a blood seal 18 located inside the blood pump 1 in order to prevent blood from entering a bearing 19 of a rotation shaft 13 in the blood pump 1, a pump controller 30 for electrically controlling the drive of the blood pump 1 via a motor cable 71, a display 40 for displaying an operation state of the aforementioned means and data thereon, a communication interface 50 for exchanging information with the outside, a power supply 33 for supplying electric power to the aforementioned means, a controller 100 for controlling the aforesaid means, and a transport section 60 for bearing the system drive section 45 portably.

The connecting section 70 comprises purge tubes 24 and 25 for connecting the blood pump 1 and the purge solution circulator 20 in the system drive section 45, the motor cable 71 for connecting the blood pump 1 and the pump controller 30, a connecting terminal 80 for connecting an internally embedded part and an externally exposed part of the connecting section 70, and a skin button section 90 for causing the internally embedded parts of the purge tubes 24 and 25 and the motor cable 71 to firmly adhere to the epidermis F of a patient. The connecting terminal 80 has a pump controller 30 and a power supply 33 for backup.

In this artificial heart, if the heart pump stops, the life of the patient may be seriously affected. On the other hand, even if advanced functions of the communication interface 50, a kinetic load detecting mechanism 31 and the like temporarily stop, it does not directly threaten the life of the patient. Regarding the blood seal 18 of the rotation shaft 13 in the blood pump 1, unless the purge solution is lost on the back of the blood seal 18, problems do not arise over the following a few hours even when the circulation of the purge solution stops. Accordingly, in this system, the pump controller 30 and the power supply 33 serving as basic functions for the rotation of the blood pump 1 need added safety. The portable artificial-heart drive system is equipped with both these basic functions, which improve the safety.

If the connecting section 70 is cut off or the system drive section 45 itself is badly damaged, however, such added safeguards provided in the system drive section 45 are useless. In view of this point, the pump controller 30 and the power supply 33 for backup are placed near the surface of the patient's body where the risks of the aforesaid accidents are low.

Figure 2:
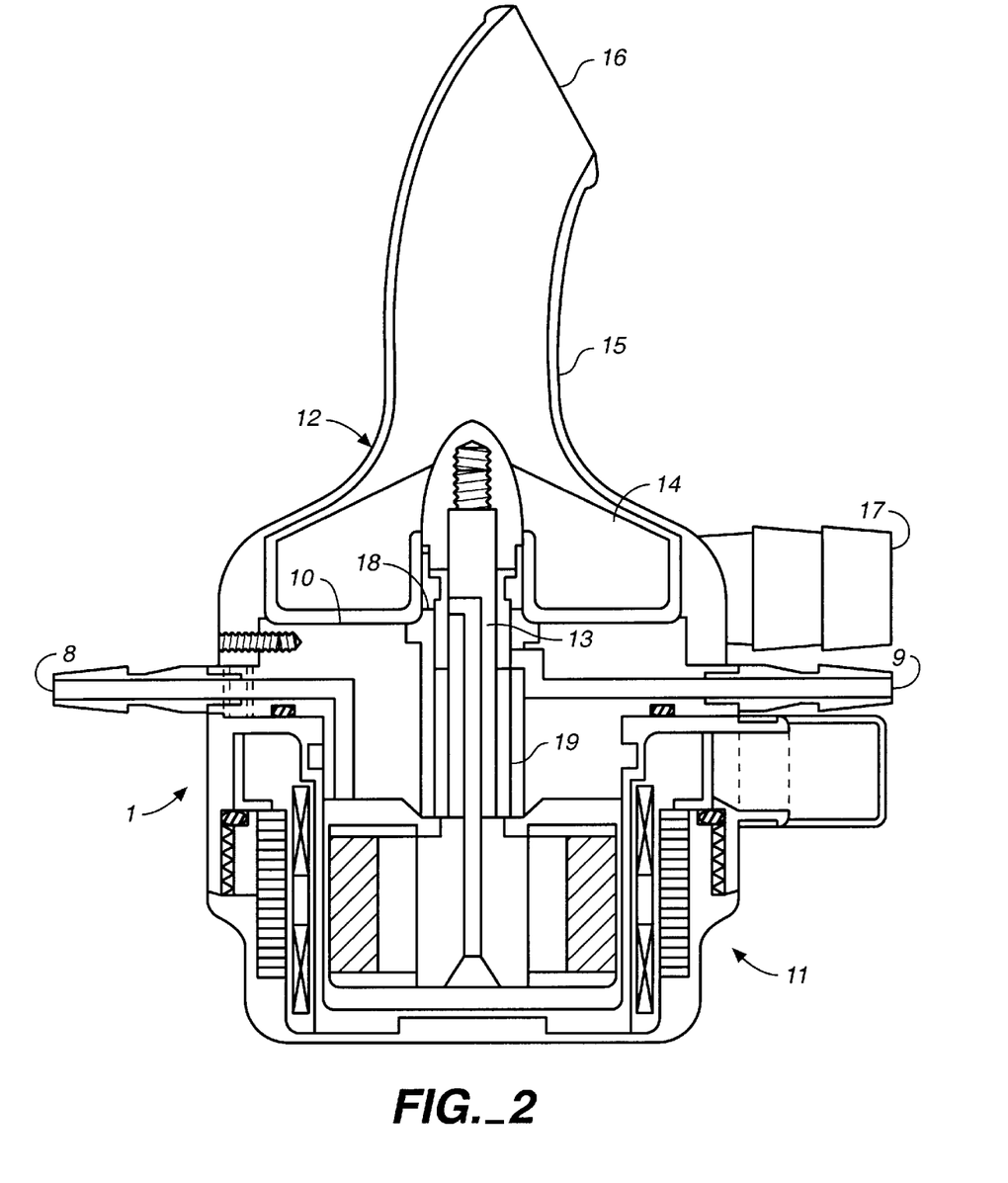
FIG. 2 is an enlarged sectional view of a blood pump shown in FIG. 1.
Figure 3:
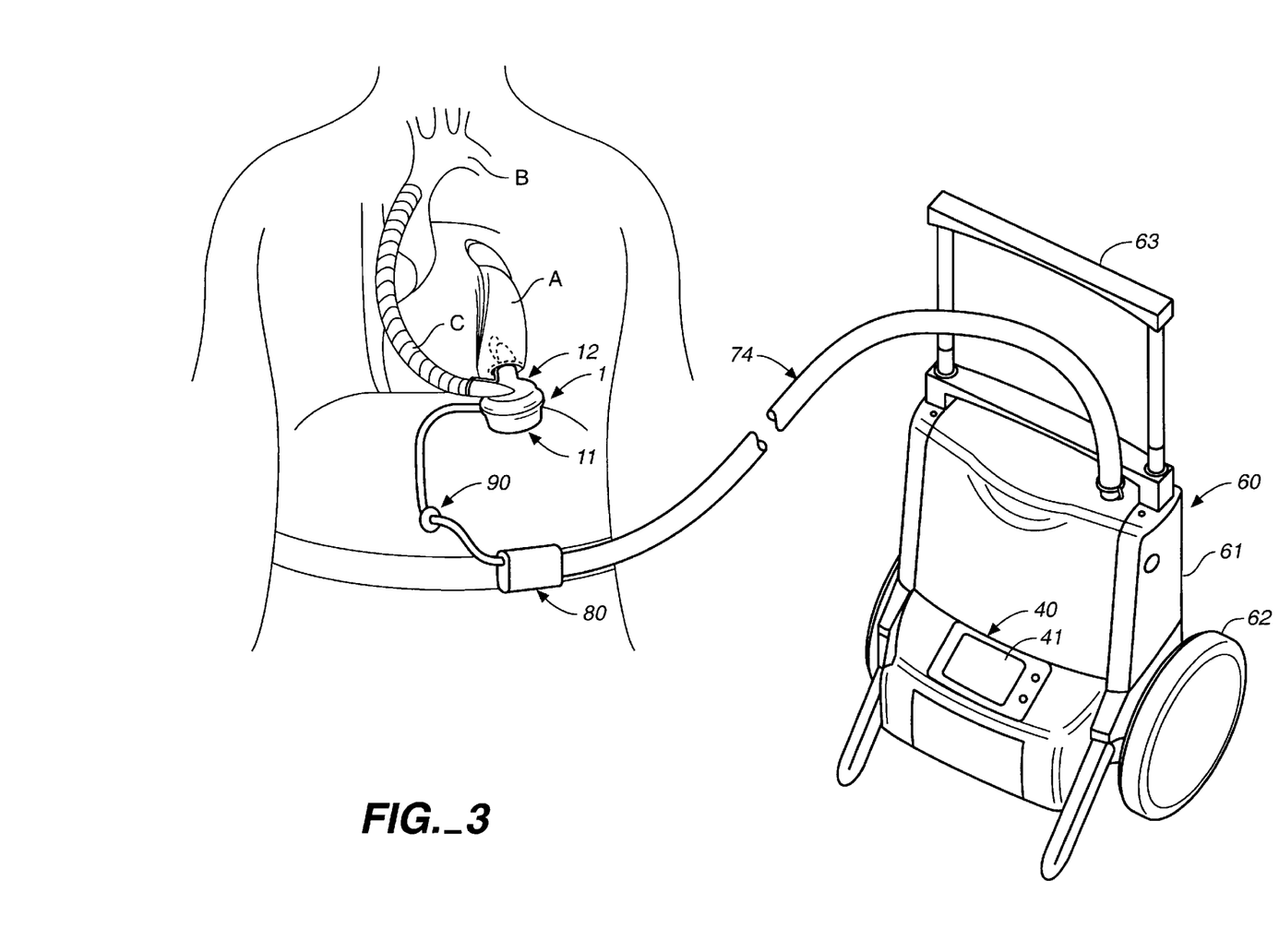
FIG. 3 is an explanatory view showing a state in which the portable artificial-heart drive system shown in FIG. 1 is implanted in a living body.

FIG. 2 shows an example of the blood pump 1, and FIG. 3 shows a case in which the portable artificial-heart drive system is implanted in the human body.

The blood pump 1 includes a pump base section 10 having a cylindrical motor portion 11, and a pump section 12 connected to the pump base section 10. The pump section 12 includes a pump vane 14 to be driven via the rotation shaft 13 extending from the motor portion 11, and a casing 15 connected to the pump base section 10 so as to cover the pump vane 14. Blood in the left ventricle A flows into the casing 15 from an inlet 16 formed at the end of the casing 15, is supplied with energy by the pump vane 14 in the casing 15, and is discharged to the aorta B via an outlet 17 formed on the side of the casing 15 and an artificial blood vessel C.

The blood seal 18 being an end-face contact type (hereinafter referred to as mechanical seal) is located between the pump base section 10 and the pump vane 14 so that it prevents the bearing 19 of the rotation shaft 13 from adhesion due to the entry of a blood ingredient. Moreover, an inlet 8 and an outlet 9 for the purge solution are formed in the pump base section 10, and connected to the purge solution circulating device, which will be described later, via the purge tubes 24 and 25. The purge solution is circulated inside the mechanical seal 18 by the purge solution circulator 20, and operates to lubricate and cool the contact surface of mechanical seal, and to remove by diffusion very small quantities of blood ingredients that enter the purge solution, whereby the contact surface of the mechanical seal 18 and the bearing 19 are always kept clean.

While a centrifugal pump is used as the blood pump 1 in this example, an axial-flow pump or a mixed flow pump are also available. Furthermore, the blood seal 18 is not limited to the mechanical seal, and other contact seals, such as an oil seal, may be available.

The system drive section 45, which includes the purge solution circulator 20 for supplying purge solution to the mechanical seal 18 located inside the blood pump 1, the pump controller 30 for electrically controlling the drive of the blood pump 1 via the motor cable 71, the display 40 for displaying the operation states of the aforementioned means and data thereon, the communication interface 50 for exchanging information with the outside, the power supply 33 for supplying electric power to the aforementioned means, and the controller 100 for controlling the aforementioned means, is constructed inside a compact housing 61, and mounted on the manual transport section 60 having wheels 62 and a handle 63.

While the transport section 60 in this example is shaped like a handcart, it may take any shape that is suited for the condition and living environment of the patient, for example, a wheel chair or a bag. Furthermore, the transport section 60 may be a motor-driven type in which the wheels 62 are equipped with a motor.

Figure 4:
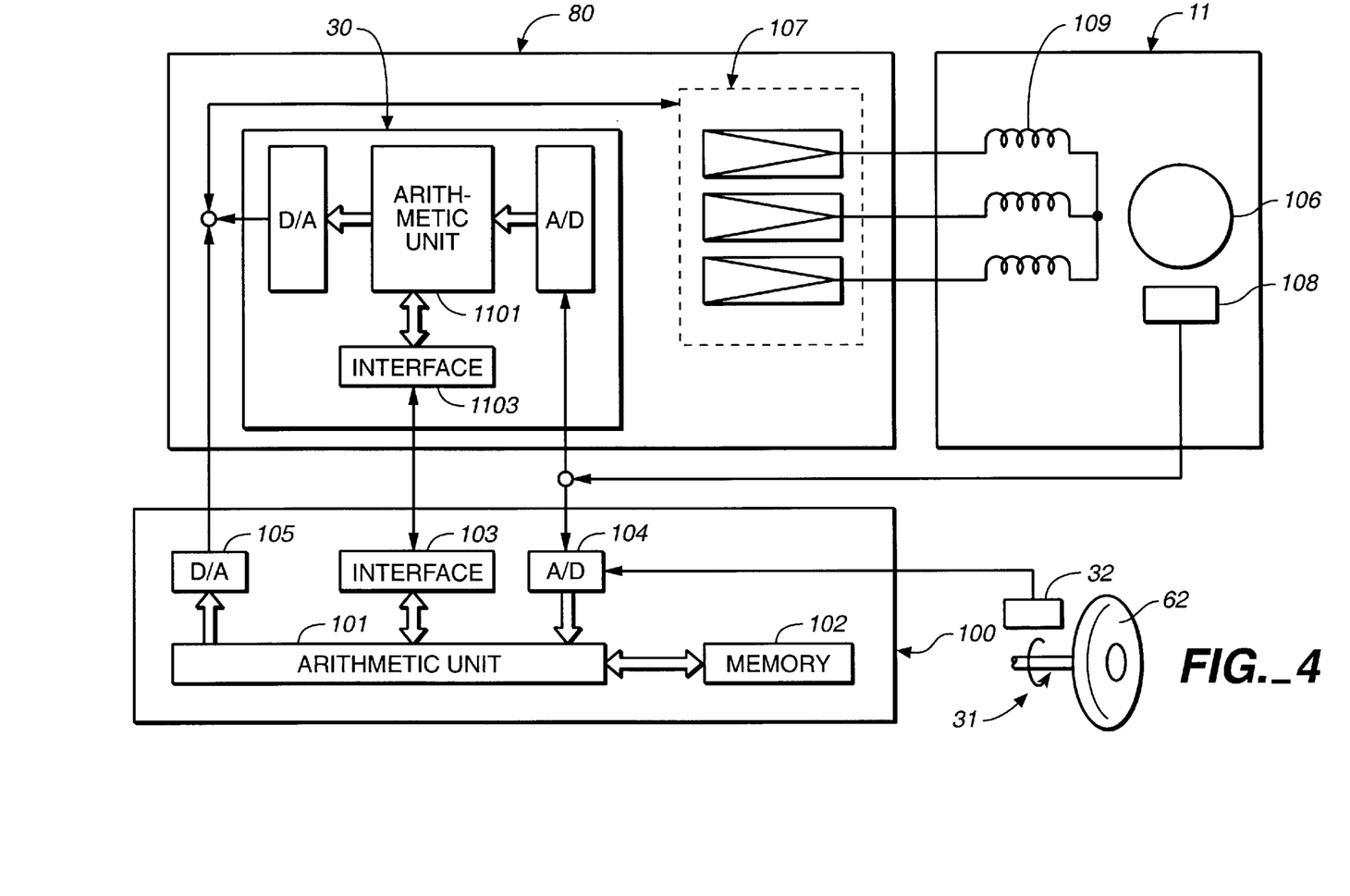
FIG. 4 is an explanatory diagram of a pump controller shown in FIG. 1.

FIG. 4 is a structural diagram of the pump controller 30.

The controller 100 is formed of a one-board microcomputer or the like that includes an arithmetic unit 101, a memory 102, and various types of interfaces 103. Output signals, which are input to the arithmetic unit 101 from sensors in the above means via an A/D converter 104, are processed according to a control program stored in a ROM of the memory 102, and the calculation result is output via a D/A converter 105. Moreover, data is exchanged with arithmetic units 101 and 1101 of the constituents via the interfaces 103 and 1103. The data is stored in a RAM of the memory 102, and displayed by the display 40.

The blood pump 1 is usually controlled by the controller 100. The control means 100 calculates a position signal corresponding to the rotational position of a rotor 106 in the pump control. The rotation of the rotor 106 is detected based on the output from a Hall sensor 108 located inside the motor portion 11 of the blood pump 1, and the arithmetic unit 101 of the controller 100 performs calculation so that the number of revolutions of the blood pump 1 is constant. Power suppliers 107 inside the connecting terminal 80 supply stator windings 109 of the motor with electric power according to the position signal.

While the number of revolutions is controlled by using the Hall sensor 108 in this embodiment, the driving can be performed without a sensor, and the control method is not limited to constant revolution control.

The backup pump controller 30 is located in the connecting terminal 80, and the controller 100 and the backup pump controller 30 mutually monitor their arithmetic units 101 and 1101 via the interfaces 103 and 1103. For example, when trouble occurs to the arithmetic unit 101 of the controller 100, the control of the blood pump 1 is switched to the backup pump controller 30, and the arithmetic unit 101 of the controller 100 is reset via the interface 103. After the arithmetic unit 101 of the controller 100 is reset and returned to a normal state, the control of the heart pump is transferred to the controller 100, and the backup pump controller 30 monitors only the arithmetic unit 101 of the controller 100. Conversely, when trouble of the arithmetic unit 1101 of the backup pump controller 30 is detected, the backup pump controller 30 is reset.

While the pump controller 30 and the power supply 33 of this example are provided in two systems, they are not limited to two systems, and may be provided in more systems.

Figure 5:
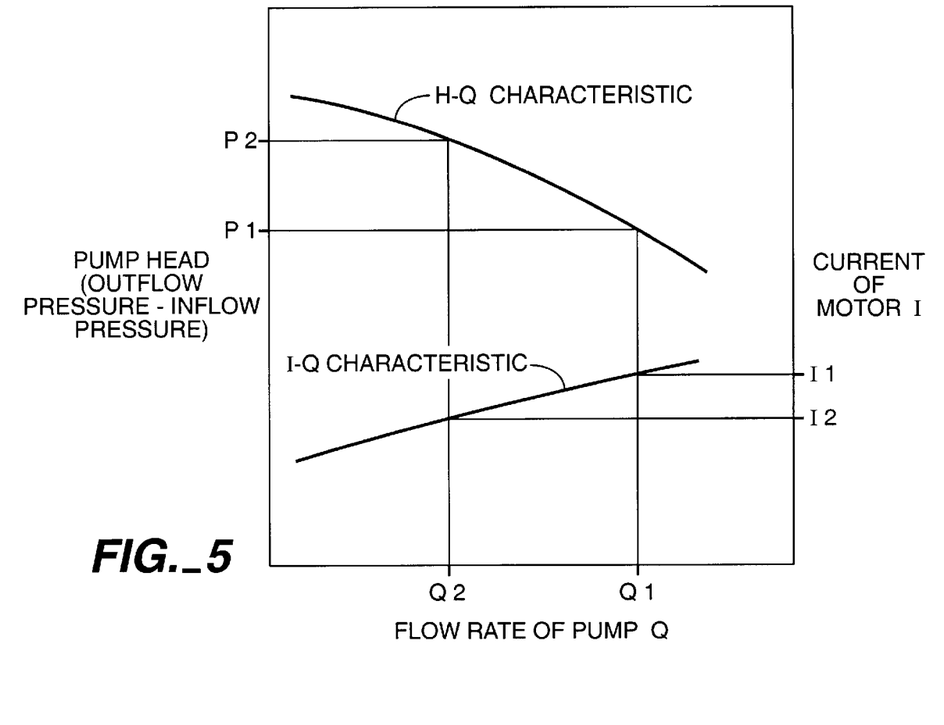
FIG. 5 is an explanatory view of a kinetic load detecting mechanism shown in FIG. 1.

The kinetic load detecting mechanism 31 is formed of a rotation detector 32 mounted on the wheel 62 of the transport section 60. The controller 100 calculates the speed of travel of the portable artificial-heart drive system based on a signal from the rotation detector 32, and increases or decreases the number of revolutions of the motor in the blood pump 1 in response to the speed of travel. Since the momentum of the patient can be easily detected, the quality of life of the patient can be improved.

Furthermore, control may be exerted by calculating the heart rate based on the change in load of the motor in the blood pump 1 depending on the heart beat of the living body and increasing or decreasing the number of revolutions of the motor in the blood pump 1 in response to the change in heart rate.

FIG. 5 explains the method of estimating the heart rate of the living body, and shows the characteristics in a case in which the centrifugal pump shown in FIG. 2 is controlled so that the number of revolutions is constant.

In this blood pump 1 that removes blood from the left ventricle A of the living body and sends the blood to the aorta B, the load on the motor portion 11 substantially varies with the change in pressure inside the left ventricle A owing to the heart beat of the living body. For example, when the difference between the internal pressure of the left ventricle A corresponding to the inflow pressure of the blood pump 1 and the pressure in the aorta B corresponding to the outflow pressure changes with the heart beat between P1 and P2, the flow rate of the blood pump 1 changes between Q1 and Q2. When the flow rate of the blood pump 1 changes between Q1 and Q2, the current value of the blood pump 1 also changes between I1 and I2. Therefore, the heart rate of the living body can be estimated by monitoring the cycle of the change in current value. Although not shown in the figure, a similar characteristic is provided in a case in which the blood pump 1 is controlled so that the current value is constant, and the heart rate of the living body can be estimated based on the change in number of revolutions of the blood pump 1.

Since the operating point of the blood pump 1 is automatically lifted or lowered according to the kinetic load of the patient, it is possible to improve the quality of life of the patient. The above-mentioned control methods may be used separately or simultaneously.

Since the detection means can be achieved in a considerably simple structure, it is possible to limit the malfunction and failure, and to thereby improve the quality of life of the patient.

Figure 6:
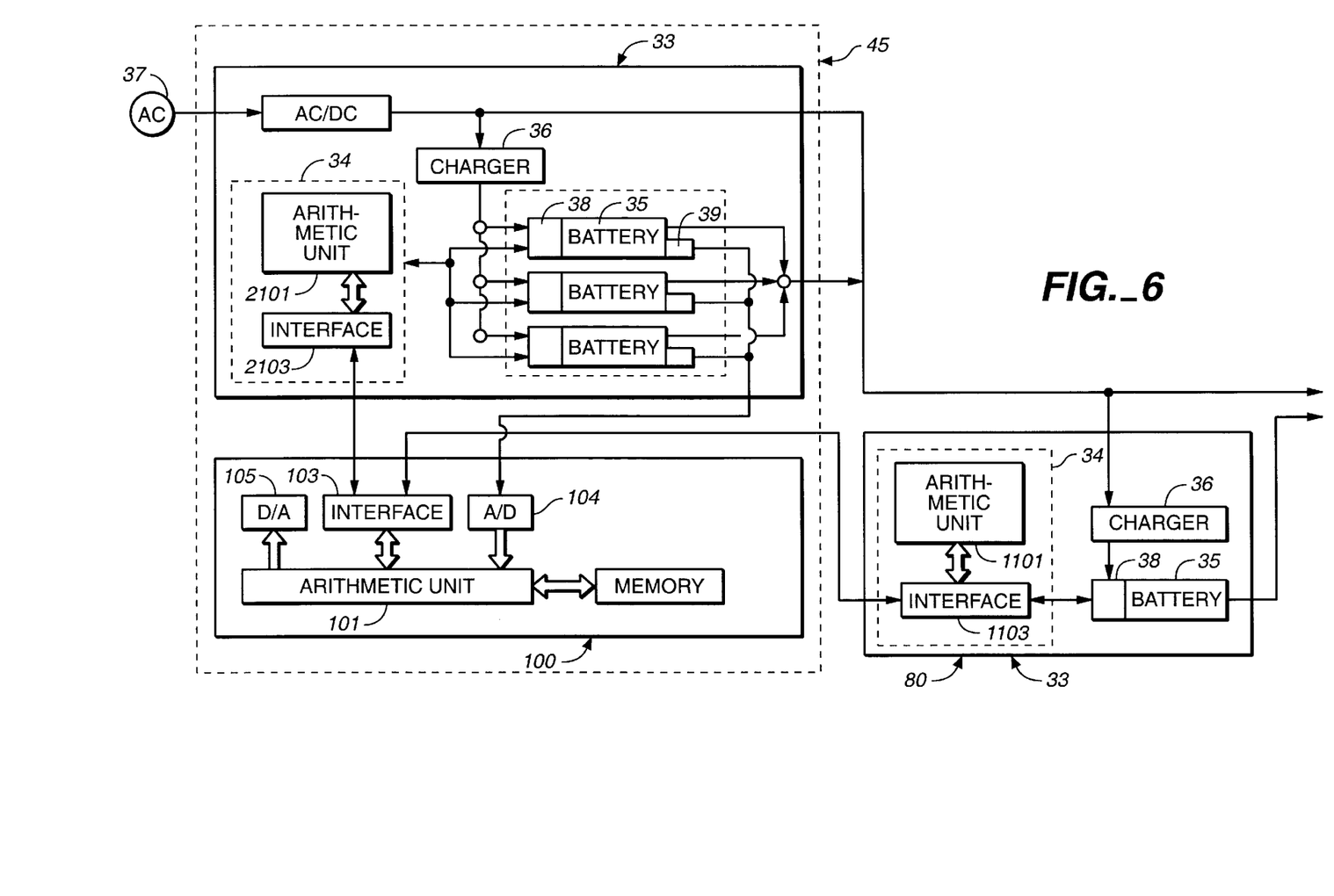
FIG. 6 is an explanatory diagram of a power supply shown in FIG. 1.

FIG. 6 is a structural diagram of the power supply 33.

The power supply 33 includes a power supply control section 34 for controlling the switching of power sources to be used and the charge and discharge of built-in batteries 35, the plural batteries 35 formed of nickel hydrogen secondary batteries or lithium ion secondary located in the system 36, and the like, and it is located in the system drive section 45 and the connecting terminal 80. In a case in which the use of an external power source 37, such as AC power source or an automobile-installed power source, is possible, the portable drive system is driven by the external power source 37, and simultaneously, the plural built-in batteries 35 are charged by the charger 36. When the external power supply 37 cannot be used, the plural batteries 35 in the system drive section 45 are sequentially used. A battery 35 in the connecting terminal 80 is used when the power supply 33 in the system drive section 45 cannot be used, for example, when the system drive section 45 is damaged. In normal operations, the power supply 33 in the system drive section 45 is used. Furthermore, when the quantity of electricity remaining in the batteries 35 in the system drive section 45 falls below a specified value, the supply of power to the means that constitute the system drive section 45 is stopped, and power is supplied only to the backup pump controller 30 in the connecting terminal 80, whereby the driving time of the portable drive system is extended.

The built-in batteries 35 are provided with battery control circuits 38, respectively, each of which monitors the remaining quantity in the battery 35, the number of times of charge and discharge, the voltage, and the like. The power supply control section 34 receives the aforesaid data from the battery control circuits 38, and sequentially and selectively controls the charge and discharge of the batteries.

The output from sensors 39, which are provided for the batteries to detect the temperatures thereof, is monitored by the controller 100, thereby preventing the combustion and explosion resulting from extraordinary heat generation of the batteries 35.

The controller 100 and the arithmetic unit 1101 of the power supply 33 mutually exchange information about operations of their constituents and monitor the operation states thereof via the interfaces 103 and 2103. For example, the arithmetic unit 1101 of the controller 100 receives, from the arithmetic unit 101 of the power supply 33, information, such as the type of power source to be used, the remaining quantity and the number of times of charge and, discharge of the batteries 35, the voltage, and the temperature of the batteries 35, and it makes a judgement on the operations. The information is displayed on the display 40. Furthermore, when the arithmetic unit 2101 of the power supply control section 34 is out of order, it is reset via the interface 2103. The configuration of the controller 100 is common to the aforementioned one, and therefore, a description thereof is omitted.

Figure 7:
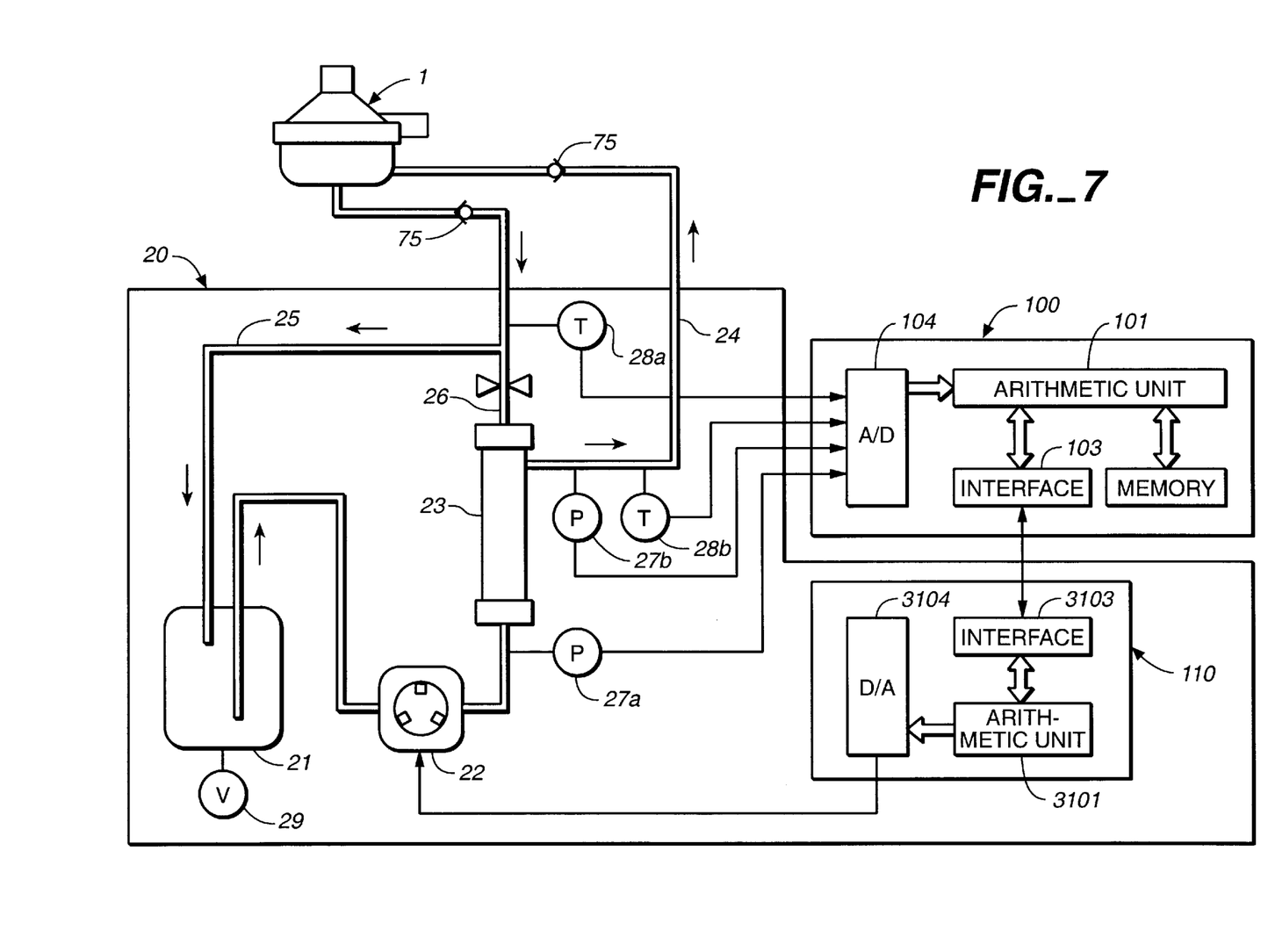
FIG. 7 is an explanatory diagram of a purge solution circulator shown in FIG. 1, FIGS. 8A–8C are explanatory views of display shown in FIG. 1.

FIG. 7 is a structural diagram of the purge solution circulator 20.

The purge solution circulator 20 supplies purge solution to the contact surface of the aforementioned mechanical seal by circulating it in order to maintain the shaft sealing of the rotation shaft 13 in the blood pump 1 with respect to blood. Purge solution with disinfectant added therein is caused by a purge solution circulating pump 22, which circulates the purge solution, to pass from a reservoir 21 for storing the purge solution through a filter 23 for filtering the purge solution. One part of the purge solution passes through the purge tube 24, flows into the blood pump 1 implanted in the body, reaches the contact surface of the mechanical seal, and then, returns to the reservoir 21 via the purge tube 25. The other part of the purge solution flowing out of the filter 23 passes through a bypass channel 26 and returns to the reservoir 21.

Moreover, valve mechanisms 75 are located on the purge tubes 24 and 25. The valve mechanisms 75 close the purge tubes 24 and 25 the moment the circulation of the purge solution stops, and holds the purge solution in the blood pump 1, thereby maintaining the function of the blood seal 18.

A protein ingredient of blood, which enters the purge solution by diffusion via a lubricating thin film on the contact surface of the mechanical seal in the blood pump 1, is filtered by the filter 23 located on the channel where the purge solution circulates. Therefore, the purge solution is always kept clean, and the bearing 19 of the rotation shaft 13 in the blood pump 1 can be prevented from seizure. Moreover, when an ultrafilter membrane is used as the filter 23, it is possible to remove bacteria, viruses, and bacteriotoxin, and to sterilize and detoxify the purge solution.

Furthermore, there is a fear that bacteria or viruses will enter the purge solution due to the exchange of purge solution or the breakage of the transport section 60, and it is preferable that the purge solution itself have a sterilizing action. Therefore, chlorination using hypochlorous acid or the like is used as a means of disinfecting the purge solution. The hypochlorous acid can sterilize almost all kinds of bacteria and viruses in low concentration, and combines with an organic matter in the living body to form an organochilorine compound, thereby performing detoxification. In addition, the reservoir 21 and the filter 23 are disinfected by adding a disinfectant in the purge solution.

Thus, the purge solution that flows in the blood pump 1 of the artificial heart is disinfected physically and chemically, which achieves double safeguards.

In order to remove bacteria, viruses and bacteriotoxin, and furthermore, to remove fibrinogen that causes the adhesion of the bearing, the pore size of the filter 23 using an ultrafilter membrane is set at a molecular weight of 340,000 or less.

Furthermore, the cross flow circulation route in which the bypass channel 26 is formed to prevent the clogging of the filter 23 serves three functions as follows.

Firstly, when the ultrafilter membrane 23 is of the hollow fiber type, since air in the fiber is automatically removed through the bypass channel 26, the filter 23 does not cause malfunction due to an air trap.

In a case in which the connecting section 70 for connecting the blood pump 1 in the artificial heart and the system drive section 45 outside the body is blocked by external force (e.g., stepped on or caught in a door), the bypass channel 26 in the purge solution circulator20 having the cross flow circulation route functions as a safety valve in such an emergency, and keeps the increase in pressure of the purge solution less than a predetermined value, thereby preventing the purge solution circulator from breaking.

In the purging circuit having a cross flow circulation route, the flow rate of the purge solution flowing in the purge solution circulator located outside the body increases by an amount corresponding to the flow rate of the purge solution passing through the bypass channel 26. Since the purge solution is cooled by heat dissipation that results from the temperature difference between the purge solution and outside air, the radiation effect of the purge solution improves as the flow rate of the purge solution increases.

Furthermore, since the purge solution decreases because it leaks from the contact surface of the mechanical seal in a very small quantity, there is a need to replace the reservoir 21 at fixed periods. Moreover, if protein adheres to the filter 23, it may cause the proliferation of bacteria, and therefore, there is also a need to replace the filter 23 at fixed periods. The reservoir 21, the purge solution circulating pump 22, and the filter 23 using an ultrafilter membrane may be combined into a unit so as to make periodical replacement considerably easy and clean.

Suited as the purge solution circulating pump 22 is a small-sized positive displacement pump that has high efficiency and high reliability, does not need a seal, and can be disinfected. In the figure, a roller pump is used, and it has a structure in which purge solution is sent out from a pipe, where it flows, by stroking the pipe from the outside. The roller pump is preferable because only the inner side of the pipe is in contact with the purge solution. Though not shown in the figure, other small pumps, such as a diaphragm pump and a gear pump, may be used.

Sensors 27*a* and 27*b* for detecting the pressure are mounted at the entrance and exit of the filter 23, and the outputs from the sensors 27*a* and 27*b* are monitored by the controller 100 via AID converter 104, whereby the choking of the purge solution circulating circuit, the clogging of the filter 23, and the like are monitored.

Furthermore, a sensor 28*a* for detecting the temperature of the purge solution, which circulates from the blood pump 1 to the purge solution circulator 20, is mounted on the purge tube 25, and the operating conditions of the purge solution circulating pump 22 are controlled so that the temperature of the purge solution does not reach the heat denaturation temperature of the protein ingredients in the blood. In this embodiment, the arithmetic unit 101 of the controller 100 calculates the operating conditions, and the arithmetic unit 3101 of the purge solution circulator control section 110 controls the purge solution circulating pump 22 according to the instructions from the controller 100 via AID converter 3104.

Still furthermore, a sensor 28*b* for detecting the temperature of the purge solution, which circulates from the purge solution circulator 20 to the blood pump 1, is mounted on the purge tube 24 to compare the temperatures of the purge solution that flows into the blood pump 1 and the purge solution that flows out therefrom, whereby the heat flow between the living body and the portable artificial-heart drive system can be grasped. By controlling the operating conditions of the purge solution circulating pump 22 so as to reduce the heat flow, it is possible to construct a portable drive system for an artificial heart that imposes little load on the living body.

The operating conditions of the purge solution circulator 20 can be grasped in more detail by adding a flow rate sensor, a blood sensor and the like besides the pressure sensor and the temperature sensor.

The reservoir 21 containing purge solution is shaped like a flexible bag, so that it can respond to its change in capacity with consumption of purge solution, in altitude with the movement of the transport section 60, and the like.

Moreover, the reservoir 21 is provided with a sensor 29 for detecting the volume of purge solution, and the output from the sensor 29 is monitored by the controller 100, thereby monitoring the leakage of the purge solution.

The controller 100 monitors the arithmetic unit 3101 of the purge solution circulator control section 110 via the interface3103, and resets it when an error occurs thereto.

Figure 8A:
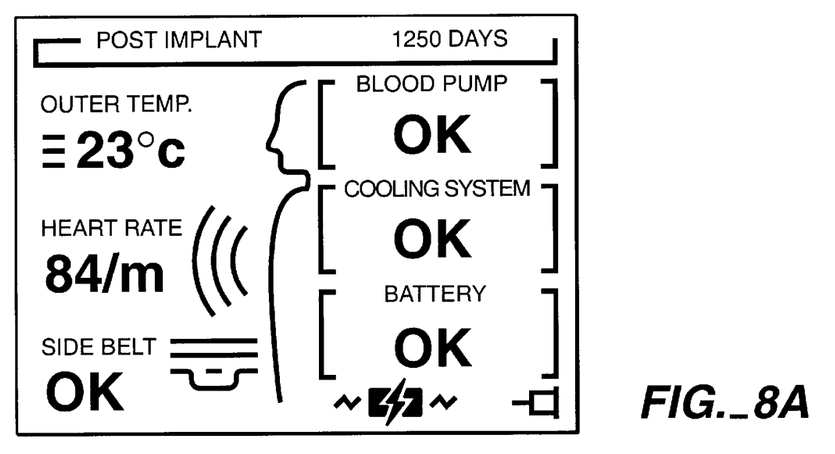

The display 40 includes a display section 41 for displaying information, and an input means (not shown) for switching displayed information and inputting data. The display section 41 always displays information about the operations of the constituents of the artificial heart that is processed by the controller 100. When the operation information deviates from set values, an alarm is given, and detailed information, such as a countermeasure, is displayed on the display section 41.

Figure 8B:
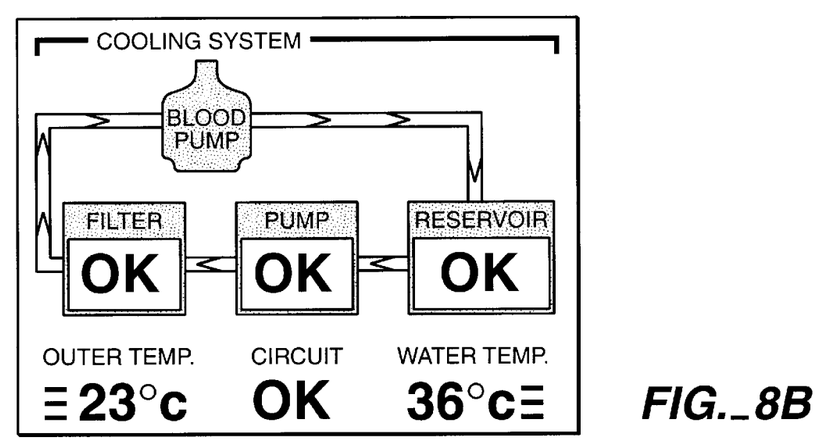
Figure 8C:
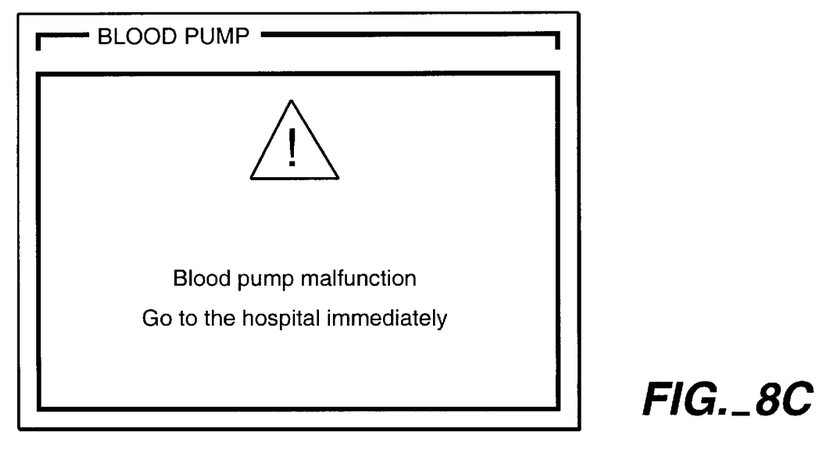

FIGS. 8(*a*) to 8(*c*) show examples of displays on the display section 41.

FIG. 8(*a*) shows a usual display state. The uppermost section indicates the number of days the present portable artificial-heart drive system has been in use. The left column indicates the outer temperature, the heart rate, and the operating state of the connecting terminal 80 in that order from the top. The right column indicates the states of the blood pump 1, the purge solution circulator 20, and the battery 35, in that order from the top. The bottom right section indicates the charge or discharge, and the use of the external power source 37. Usually, basic information about the operations mentioned above is displayed, and more detailed information about the operations of the constituents may be displayed through the input means.

FIG. 8(*b*) shows detailed operation states of the purge solution circulator 20. The upper section indicates the operation states of the blood pump 1, the reservoir 21, the purge solution circulating pump 22, and the filter 23 that constitute the purge solution circulator 20, and the purge tubes 24 and 25. The lower section indicates, from the left, the outer temperature, the operation state of the arithmetic unit 101 in the purge solution controller 100, and the temperature of the purge solution.

When abnormal conditions are encountered, the message shown in FIG. 8(*c*) is displayed, and details of the abnormal conditions may be displayed by switching through the input means (not shown).

In addition, operating parameters may be changed through the input means.

The communication interface 50 has a connecting terminal for connection to a telephone line, and- can make connection to a computer in a hospital or the like. The portable artificial-heart drive system can be controlled and monitored by a computer in the hospital. By incorporating the mobile communication interface 50, such as a portable telephone, information about the portable artificial-heart drive system is appropriately transferred to the hospital or the like, and appropriate instructions are transferred back. Therefore, the safety of life of the patient outside the hospital is further increased.

Figure 9:
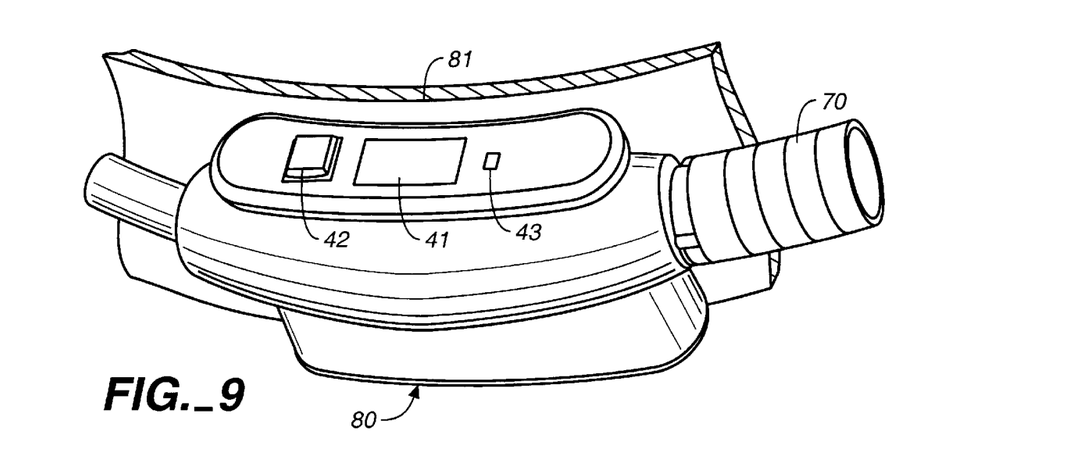
FIG. 9 is an explanatory view of a connecting terminal shown in FIG. 1.

FIG. 9 shows an example of the connecting terminal 80.

The connecting terminal 80 connects the internally embedded part and the externally exposed part of the connecting section 70. The connecting terminal 80 is fixed to a belt-like stomach band 81. Since the externally exposed part of the connecting section 70 is expandable, external, force caused by movement of the body is not directly transmitted to the internally embedded part of the connecting section 70.

Furthermore, the connecting terminal 80 has a display section 41 on which information, such as the number of revolutions of the motor in the blood pump 1 and the amount of electricity in the battery, is sequentially displayed by switching using a control button 42. When an error occurs, it is announced by the illumination of an error indicator 43 and an alarm.

Still furthermore, the pump controller 30 and the power supply 33 for backup are built in the connecting terminal 80. When the system drive section 45 stops because of any trouble, the blood pump 1 is driven by the backup pump controller 30 and the backup power supply 33 inside the connecting terminal 80.

Though not shown, the externally exposed part of the connecting section 70 is connected so that it splits at the connecting terminal 80. Moreover, the purge tubes 24 and 25 and backup terminals of the motor cable 71 are also built in the connecting terminal 80, and easy access is possible even during the maintenance of the system drive section 45.

Figure 10:
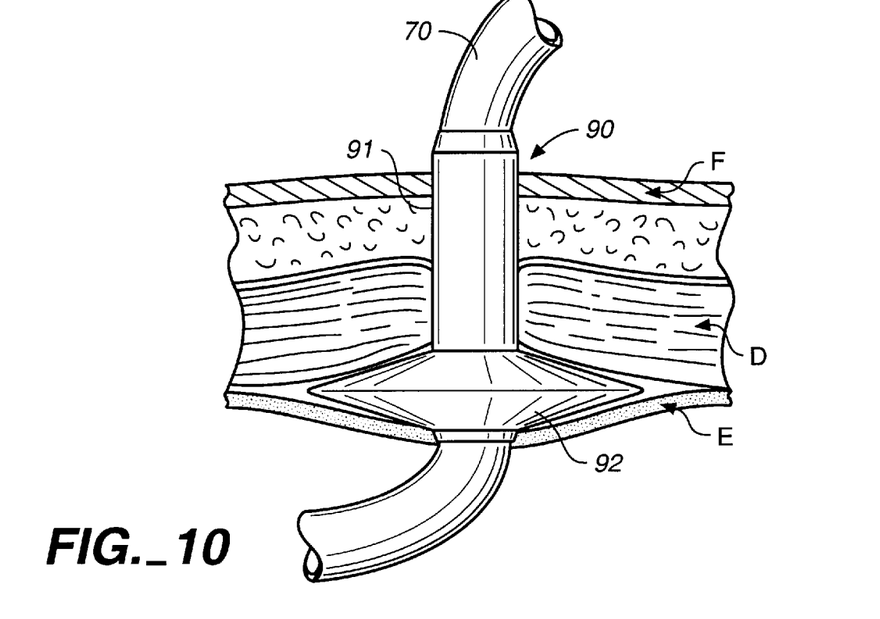
FIG. 10 is an enlarged sectional view of a skin button section shown in FIG. 1.

FIG. 10 shows an example of the skin button section 90. The skin button section 90 is a structure composed of a plurality of carbon fibers having many pores on the surface thereof, and includes a cylindrical portion 91 and a flange portion 92. The flange portion 92 is located between the musculus rectus abdominis D and the vagina musculi recti abdominis E, and one end of the cylindrical portion 91 reaches the epidermis F. The skin button section 90 firmly adheres to the tissue that is in contact therewith, prevents the separation of the connecting section 70 due to the movement of the body, and thereby avoids infectious diseases via the connecting section 70.

Figure 11:
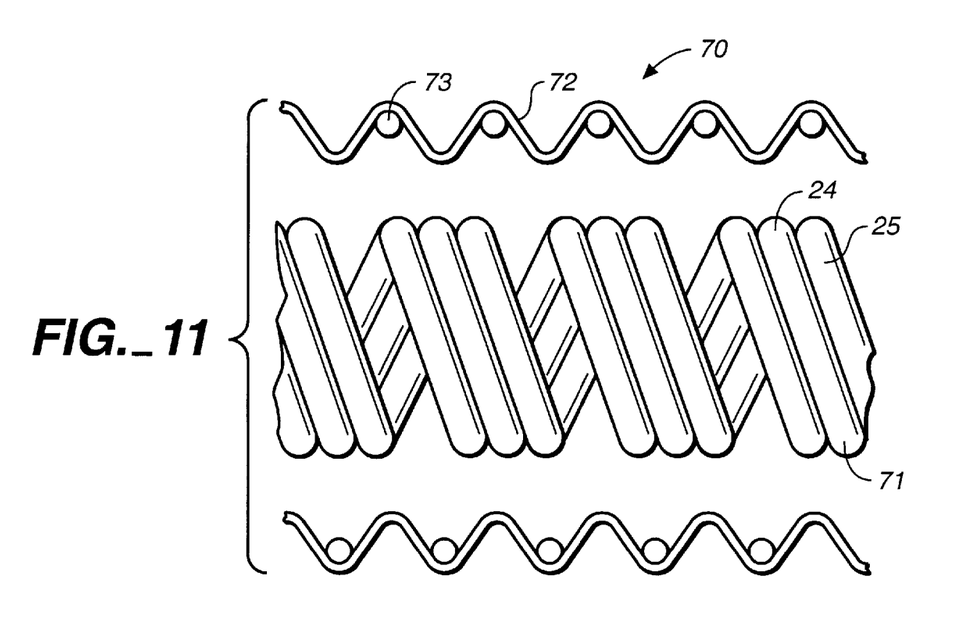
FIG. 11 is an enlarged sectional view of a connecting section shown in FIG. 1.

FIG. 11 shows an example of the connecting section 70. The connecting section 70 includes the purge tubes 24 and 25, the motor cable 71, and a protective tube 72 for covering them. The purge tubes 24 and 25 and the motor cable 71 are helically formed, the protective tube 72 is shaped like a bellows, and both are expandable so as not to hinder the movement of the body of the patient. The expansion amount of the protective tube 72 is set smaller than that of the purge tubes 24 and 25 and the motor cable 71, and the maximum expansion amount of the protective tube 72 limits the expansion amount of the connecting section 70, whereby the purge tubes 24 and 25 and the motor cable 71 are prevented from breaking. Furthermore, the protective tube 72 is made of a material that is resistant to breakage, such as Kevlar fiber, and the surface thereof is waterproofed. Still furthermore, a plurality of circular rings 73 made of metal, resin or the like are embedded in the protective tube 72 in order to prevent the purge tubes 24 and 25 and the motor cable 71 from deforming and breaking when load directly acts on the connecting section 70.

As mentioned above, according to the present invention, since the pump controller, the purge solution circulator, the controller, the display, the communication interface, and the power supply are made compact and mounted on the transport section, the life outside the hospital is permitted.

Furthermore, a plurality of pump controller and power supply make it possible to maintain safe blood circulation under abnormal conditions.

The addition of disinfectant in the purge solution makes it possible to prevent blood from coagulating, to remove and sterilize miscellaneous bacteria as well as the ultrafilter, and to thereby circulate a clean p urge solution.

The number of revolutions of the blood pump can be controlled by the controller in accordance with the kinetic load, blood circulation can be always kept stable and safe, and the drive condition of the artificial heart can be monitored through the display. Therefore, the patient can manage himself or herself, and the patient or a third person can respond to abnormal conditions. Moreover, since the communication interface permits the doctor and the hospital to quickly respond to abnormal conditions of the artificial heart, the safety of life outside the hospital is substantially improved.

The connecting terminal attached to a belt like a stomach band permits the patient to live everyday life without worrying about its appearance. This also makes it possible to reduce the influence of the body movement on the epidermis.

Furthermore, since the skin button section formed of carbon fibers is embedded in the body near the epidermis, it firmly adheres to cells, thereby preventing infectious diseases.

In addition, since the connecting section has both expandability and strength, ease of use and safety can be achieved.

While the present invention has been described in its preferred embodiment applied to an artificial heart, various modifications and changes of the embodiment may be made in the present invention within the technical scope thereof, and the invention may be applied to a pump-oxygenator, artificial dialysis, and the like.

What is claimed is:

1. A portable artificial-heart drive system, comprising:
   a blood pump to cause blood to flow, said blood pump comprising:
     a motor portion having a drive shaft to drive an artificial heart of a patient,
     a bearing,
     a rotation shaft extending from said motor portion and supported by said bearing,
     a pump vane driven via said rotation shaft,
     a blood seal for preventing a blood ingredient from entering said bearing, and
     a casing connected to said motor portion and covering said pump vane;
   a system drive section comprising:
     a purge solution circulator to supply purge fluid solution by circulating to a contact portion of said blood seal to maintain shaft sealing of said rotation shaft with respect to blood of the patient,
     a motor cable,
     a pump controller to electrically control said motor portion in said blood pump via said motor cable,
     a power supply to supply electric power to said pump controller and said purge solution circulator,
     a display to display operating states of at least one of said pump controller, said power supply and said purge solution circulator and data thereon,
     a communication interface to exchange information with an external device, and a controller to control said display, said communication interface, said pump controller, said power supply and said purge solution circulator;

a movable transport section accommodating said system drive section; and a connection unit comprising:
   a connecting section to connect said blood pump and said system drive section, and
   a skin button section to secure said connecting section on the epidermis of the patient.

2. A portable artificial-heart; drive system according to claim 1, wherein said blood seal comprises one of a mechanical seal and an oil seal.

3. A portable artificial-heart drive system according to claim 1, wherein each of said purge solution circulator, pump controller, display, controller and communication interface has a respective priority, wherein said power supply supplies electric power only to at least one of said purge solution circulator, pump controller, display, controller and communication interface if the respective priority is high and if a quantity of electric power remaining in said power supply falls below a specified value.

4. A portable artificial-heart drive system according to claim 3, wherein pump controller has the high priority.

5. A portable artificial-heart drive system according to claim 1, wherein said system drive section comprises at least two pump controllers and respective power supplies.

6. A portable artificial-heart drive system according to claim 1, further comprising:
   a second pump controller and a second power supply,
   wherein said second pump controller and second power supply are disposed outside of said transport section.

7. A portable artificial-heart drive system according to claim 1, wherein said purge solution circulator comprises:
   a reservoir to store the purge solution;
   a purge solution circulating pump,
   a filter, and
   a purge solution circulation route for connecting said reservoir, said purge solution circulation pump and said filter among one another,
   wherein said purge solution circulating pump circulates the purge solution between said reservoir and said blood seal,
   wherein said filter filters the purge solution,
   wherein said purge solution circulator circulates the purge solution inside said blood pump via said filter.

8. A portable artificial-heart drive system according to claim 7, wherein said purge solution comprises:
   a solution selected from the group consisting of pure water and physiological saline, and
   a disinfectant for sterilizing the purge solution.

9. A portable artificial-heart drive system according to claim 7, wherein said purge solution circulator further comprises a bypass channel wherein said reservoir has an inlet and an outlet, wherein said outlet is in communication with said purge solution circulating pump, wherein said purge solution circulating pump is in communication with said filter, wherein said inlet is in communication with said bypass channel and wherein said bypass channel is in communication with said filter.

10. A portable artificial-heart drive system according to claim 7, wherein said purge solution circulating pump, said filter, and said reservoir are combined into a unit.

11. A portable artificial-heart drive system according to claim 7, wherein said reservoir comprises a flexible material.

12. A portable artificial-heart drive system according to claim 7, wherein said purge solution circulator further comprises at least one pressure sensor disposed at one of an inlet and outlet of said filter.

13. A portable artificial-heart drive system according to claim 7, wherein said purge solution circulator further comprises at least one temperature sensor.

14. A portable artificial-heart drive system according to claim 1, wherein said controller comprises a kinetic load detecting mechanism to detect the kinetic load of the patient using said portable drive system, and wherein said controller controls the operating condition of said blood pump according to the output from said kinetic load detecting mechanism.

15. A portable artificial-heart drive system according to claim 14, wherein said kinetic load detecting mechanism detects a moving speed of said transport section.

16. A portable artificial-heart drive system according to claim 14, wherein said kinetic load detecting mechanism detects a load change of said motor portion in said blood pump, the load change synchronizing with the heart rate of the living body.

17. A portable artificial-heart drive system according to claim 14, wherein said kinetic load detecting mechanism comprises:
   a speed detector to detect a speed of said transport section, and
   a heart rate detector to detect the heart rate of the patient.

18. A portable artificial-heart drive system according to claim 16, wherein said kinetic load detecting mechanism detects a change in current value of said motor portion in said blood pump, and detects the kinetic load of the patient based on an estimated heart rate.

19. A portable artificial-heart drive system according to claim 16, wherein said kinetic load detecting mechanism detects a change in number of revolutions of said motor portion in said blood pump, and detects the kinetic load of the patient based on an estimated heart rate.

20. A portable artificial-heart drive system according to claim 1, wherein said display displays operating states of said said portable artificial-heart drive system, and provides an alarm when deviation from a set value arises.

21. A portable artificial-heart drive system according to claim 1, wherein said communication interface exchanges information between the patient and one of a hospital and a doctor.

22. A portable artificial-heart; drive system according to claim 1, further comprising:
   a connecting terminal arranged on a belt-like stomach band worn by the patient; and
   a motor cable connecting said blood pump, said connecting terminal and said pump controller,
   wherein said connecting section comprises first and second purge tubes for connecting said blood pump and said purge solution circulator, said motor cable.

23. A portable artificial-heart drive system according to claim 22, wherein said connecting section further comprises a bellow-like protective tube, wherein said first and second purge tubes and said motor cable are helically shaped, and said bellows-like protective tube covers said first and second purge tubes and said motor cable, so that said connecting section is expandable.

24. A portable artificial-heart; drive system according to claim 23, wherein an expansion amount of said protective tube is smaller than that of said first and second purge tubes and said motor cable in said connecting section.

25. A portable artificial-heart drive system according to claim 23, wherein said protective tube comprises a plurality of circular rings embedded therein.

26. A portable artificial-heart drive system according to claim 22, wherein said first and second purge tubes comprise a valve mechanism for blocking the flow of the purge solution.

27. A portable artificial-heart drive system according to claim 26, wherein said valve mechanism is disposed between said connecting terminal and said blood pump.

28. A portable artificial-heart drive system according to claim 22, wherein said connecting terminal comprises at least one system of pump controller and a power supply.

29. A portable artificial-heart drive system according to claim 1, wherein said skin button section comprises a carbon fiber structure having many air spaces on the surface thereof, and is implanted inside the epidermis F of the patient.

30. A portable artificial-heart drive system according to claim 1, wherein said transport section comprises a mount having a wheel for portably bearing said system drive section located outside the body, and is automatically and manually carried along with the patient.

31. A portable artificial-heart drive system according to claim 30, wherein said transport section comprises a waterproof and anti-contamination structure for preventing contaminants from entering said system drive section.

32. A portable artificial-heart drive system according to claim 30, wherein said transport section comprises a shock-absorbing structure so that vibrations and shocks caused by movement are not transmitted to said system drive section.

33. A portable artificial-heart drive system according to claim 1, wherein said power supply comprises a plurality of power sources, wherein said plurality of power sources comprises at least one of a commercial AC power source, an automobile-installed power source, and a secondary battery built in said transport section, wherein said power supply comprises a switch to select at least one of said plurality of sources.

* * * * *

UNITED STATES PATENT AND TRADEMARK OFFICE
CERTIFICATE OF CORRECTION

PATENT NO. : 6,123,726
DATED : September 26, 2000
INVENTOR(S) : Toshio Mori, et al.

Page 1 of 1

It is certified that error appears in the above-identified patent and that said Letters Patent is hereby corrected as shown below:

Column 15,
Line 11, delete ";".

Signed and Sealed this

Twenty-first Day of August, 2001

Attest:

*Nicholas P. Godici*

NICHOLAS P. GODICI
*Attesting Officer*     *Acting Director of the United States Patent and Trademark Office*